US010078076B2

(12) United States Patent
Palmer et al.

(10) Patent No.: US 10,078,076 B2
(45) Date of Patent: Sep. 18, 2018

(54) IMMUNE MONITORING TO PREDICT AND PREVENT INFECTION

(71) Applicant: Duke University, Durham, NC (US)

(72) Inventors: Scott M. Palmer, Durham, NC (US); Kent J. Weinhold, Durham, NC (US); Chi Wei Cliburn Chan, Durham, NC (US); Laurie D. Snyder, Durham, NC (US)

(73) Assignee: Duke University, Durham, NC (US)

( * ) Notice: Subject to any disclaimer, the term of this patent is extended or adjusted under 35 U.S.C. 154(b) by 114 days.

(21) Appl. No.: 15/039,679

(22) PCT Filed: Nov. 26, 2014

(86) PCT No.: PCT/US2014/067726
§ 371 (c)(1),
(2) Date: May 26, 2016

(87) PCT Pub. No.: WO2015/081267
PCT Pub. Date: Jun. 4, 2015

(65) Prior Publication Data
US 2016/0377602 A1 Dec. 29, 2016

Related U.S. Application Data

(60) Provisional application No. 62/014,906, filed on Jun. 20, 2014, provisional application No. 61/908,890, filed on Nov. 26, 2013.

(51) Int. Cl.
*G01N 33/50* (2006.01)
(52) U.S. Cl.
CPC ... *G01N 33/5091* (2013.01); *G01N 2333/525* (2013.01); *G01N 2333/55* (2013.01); *G01N 2333/57* (2013.01); *G01N 2333/70596* (2013.01); *G01N 2800/50* (2013.01); *G01N 2800/52* (2013.01)
(58) Field of Classification Search
CPC .... A61K 39/12; A61K 39/245; A61K 39/395; C07K 7/00
See application file for complete search history.

(56) References Cited

U.S. PATENT DOCUMENTS

| 8,425,898 B2 | 4/2013 | Sampson et al. |
| 2008/0112949 A1 | 5/2008 | Winsor-Hines et al. |
| 2012/0093848 A1 | 4/2012 | Lian et al. |
| 2012/0288850 A1 | 11/2012 | Soethout et al. |

FOREIGN PATENT DOCUMENTS

CN 102297968 12/2011

OTHER PUBLICATIONS

Fuhrmann, S., et al. Cyclosporin A and tacrolimus reduce T-cell polyfunctionality but not interferon-gamma responses directed at cytomegalovirus. Immunol. vol. 136:4. Aug. 2012. pp. 408-413.
Hoegh-Peterson, M., et al. Low cytomegalovirus-specific T-cell counts at reactivation are associated with progression to high-level viremia or disease in seropositive recipients of hematopoietic cell grafts from seropositibe but not seronegative donors. Cytotherapy. vol. 14:2. Feb. 2012. pp. 194-204.
Lacey, S.F., et al. Functional comparison of T cells recognizing cytomegalosvirus pp65 and intermediate-early antigen polypeptides in hematopoietic stem-cell transplant and solid organ transplant recipients. J Infect. Dis. vol. 194. 2006. pp. 1410-1421.
Snyder, L.D., et al., Polyfunctional T-cell signatures to predict protection from cytomegalovirus after lung transplantation. Am. J. Respir. Crit. Care Med. vol. 193:1. Sep. 2015. pp. 78-85.
Zhou, W. et al. Imoact of donor CMV status on viral infection and reconstitution fo multifunction CMV-specific T cells in CMV-positive transplant recipients Blood. vol. 113:25. Jun. 18, 2009. pp. 6465-6476.
Bunde, T., Kirchner, A., Hoffmeister, B., Habedank, D., Hetzer, R., Cherepney, G., et al., Protection from cytomegalovirus after transplantation is correlated with immediate early 1-specific CD8 T cells. J Exp Med. 2005;201(7):1031-6.
Chiereghin, A., Gabrielli, L., Zanfi, C., Petrisli, E., Lauro, A., Piccirilli, G., et al., Monitoring cytomegalovirus T-cell immunity in small bowel/multivisceral transplant recipients. Transplant Proc. 2010;42(1):69-73. Epub Feb. 23, 2010.
Ciuffreda, D., Comte, D., Cavassini, M., Giostra, E., Buhler, L., Perruchoud, M., et al., Polyfunctional HCV-specific T-cell responses are associated with effective control of HCV replication. Eur J Immunol. 2008;38(10):2665-77. Epub Oct. 30, 2008.
de Silva T.I, Peng, Y., Leligdowicz, A., Zaidi, I., Li, L., Griffin, H., et al., Correlates of T-cell-mediated viral control and phenotype of CD8(+) T cells in HIV-2, a naturally contained human retroviral infection. Blood. 2013;121(21):4330-9. Epub Apr. 6, 2013.
Egli, A., Humar, A., Kumar, D. State-of-the-art monitoring of cytomegalovirus-specific cell-mediated immunity after organ transplant: a primer for the clinician. Clin Infect Dis. 2012;55(12):1678-89. Epub Sep. 20, 2012.
Gerna, G., Lilleri, D., Chiesa, A., Zelini, P., Furione, M., Comolli, G., et al., Virologic and immunologic monitoring of cytomegalovirus to guide preemptive therapy in solid-organ transplantation. Am J Transplant. 2011;11(11):2463-71. Epub Aug. 11, 2011.
Kannanganat, S., Ibegbu, C., Chennareddi, L., Robinson, H.L., Amara, R.R., Multiple-cytokine-producing antiviral CD4 T cells are functionally superior to single-cytokine-producing cells. J Virol. 2007;81(16):8468-76. Epub Jun. 8, 2007.
Kotton, C.N., et al., Updated International Consensus Guidelines on the Management of Cytomegalovirus in Solid-Organ Transplantation. Transplantation. 2013;96(4):333-60. Epub Jul. 31, 2013.

(Continued)

*Primary Examiner* — Bao Q Li
(74) *Attorney, Agent, or Firm* — Andrus Intellectual Property Law, LLP

(57) ABSTRACT

Methods of evaluating the risk of infection after transplantation or immunosuppression in a subject are provided. Methods of determining whether a subject should be treated prophylactically with an anti-microbial agent are also provided herein. Kits for performing the methods described herein are also provided.

19 Claims, 5 Drawing Sheets

(56) References Cited

OTHER PUBLICATIONS

Kumar, D., et al. Cell-mediated immunity to predict cytomegalovirus disease in high-risk solid organ transplant recipients. Am J Transplant. 2009;9(5):1214-22.

Makedonas, G., et al., Polyfunctional analysis of human t cell responses: importance in vaccine immunogenicity and natural infection. Springer Semin Immunopathol. 2006;28(3):209-19.

Manuel, O., et al., Assessment of cytomegalovirus-specific cell-mediated immunity for the prediction of cytomegalovirus disease in high-risk solid-organ transplant recipients: a multicenter cohort study. Clin Infect Dis. 2013;56(6):817-24. Epub Dec. 1, 2012.

Nickel, P., et al. High levels of CMV-IE-1-specific memory T cells are associated with less alloimmunity and improved renal allograft function. Transpl Immunol. 2009;20(4):238-42. Epub Nov. 27, 2008.

Paraskeva, M., et al. Cytomegalovirus replication within the lung allograft is associated with bronchiolitis obliterans syndrome. Am J Transplant. 2011;11(10):2190-6. Epub Jul. 29, 2011.

Pipeling, M.R., et al. Differential CMV-specific CD8+ effector T cell responses in the lung allograft predominate over the blood during human primary infection. J Immunol. 2008;181(1):546-56.

Precopio, M.L., et al. Immunization with vaccinia virus induces polyfunctional and phenotypically distinctive CD8(+) T cell responses. J Exp Med. 2007;204(6):1405-16.

Scheinberg, P., et al., "The transfer of adaptive immunity to CMV during hematopoietic stem cell transplantation is dependent on the specificity and phenotype of CMV-specific T cells in the donor," Blood, 2009, pp. 5071-5080, vol. 114.

Sester, U., et al. Differences in CMV-specific T-cell levels and long-term susceptibility to CMV infection after kidney, heart and lung transplantation. Am J Transplant. 2005;5(6):1483-9. Epub May 13, 2005.

Sester, M., et al. Levels of virus-specific CD4 T cells correlate with cytomegalovirus control and predict virus-induced disease after renal transplantation. Transplantation. 2001;71(9):1287-94. Epub Jun. 9, 2001.

Sester, M., et al., Dominance of virus-specific CD8 T cells in human primary cytomegalovirus infection. Journal of the American Society of Nephrology : JASN. 2002;13(10):2577-84. Epub Sep. 20, 2002.

Snyder, L.D., et al., Cytomegalovirus pneumonitis is a risk for bronchiolitis obliterans syndrome in lung transplantation. Am J Respir Crit Care Med. 2010;181(12):1391-6. Epub Feb. 20, 2010.

Snyder, L.D., et al., Polyfunctional cytomegalovirus-specific immunity in lung transplant recipients receiving valganciclovir prophylaxis. Am J Transplant. 2011;11(3):553-60. Epub Jan. 12, 2011.

Tu, W., et al., T-cell immunity to subclinical cytomegalovirus infection reduces cardiac allograft disease. Circulation. 2006;114(15):1608-15. Epub Oct. 4, 2006.

van Lier, R.A., et al., Human CD8(+) T-cell differentiation in response to viruses. Nat Rev Immunol. 2003;3(12):931-9. Epub Dec. 4, 2003.

Weseslindtner, L., et al., Prospective analysis of human cytomegalovirus DNAemia and specific CD8+ T cell responses in lung transplant recipients. Am J Transplant. 2012;12(8):2172-80. Epub May 3, 2012.

Westall, G.P., et al., Bronchiolitis obliterans syndrome and early human cytomegalovirus DNAaemia dynamics after lung transplantation. Transplantation. 2003;75(12):2064-8. Epub Jun. 28, 2003.

Westall, G.P., Mifsud, N.A., Kotsimbos, T., Linking CMV serostatus to episodes of CMV reactivation following lung transplantation by measuring CMV-specific CD8+ T-cell immunity. Am J Transplant. 2008;8(8):1749-54. Epub Jun. 19, 2008.

Zuk, D.M., et al., An international survey of cytomegalovirus management practices in lung transplantation. Transplantation. 2010;90(6):672-6. Epub Jun. 29, 2010.

International Search Report and Written Opinion for International Application PCT/US14/067726 dated Mar. 10, 2015.

IMMUNE MONITORING TO PREDICT AND PREVENT INFECTION

CROSS-REFERENCE TO RELATED APPLICATIONS

This patent application is a national stage filing under 35 U.S.C. 371 of International Application No. PCT/US2014/1067726, filed Nov. 26, 2014, which claims the benefit of priority of U.S. Provisional Patent Application No. 61/908,890, filed Nov. 26, 2013 and U.S. Provisional Patent Application No. 62/014,906, filed Jun. 20, 2014, all of which are incorporated herein by reference in their entireties.

INTRODUCTION

Infection, particularly reactivation of latent viruses, is a common health complication for immunocompromised patients, such as those who have undergone an organ transplant. Infection is a major cause of organ transplantation failure. Organ transplant patients routinely receive immunosuppressive therapy to reduce the chance of organ rejection. The recipient of a transplant or a donor of a transplanted organ may be a source of an infectious agent such as a latent virus. In many cases, transplant recipients are treated prophylactically with anti-microbial pharmaceuticals to prevent infection after transplantation. The treatments are not tolerated well by some recipients and others may have reactivation of an infectious agent after the treatment is stopped.

Cytomegalovirus (CMV) infection is the most common viral infection in lung transplant recipients. A majority of individuals are exposed to CMV in early childhood but the virus persists as a latent infection. In the setting of organ transplantation and/or immunosuppression, CMV can reactivate leading to a viral syndrome or disease in the transplanted organ. The development of post-transplant CMV infection or pneumonia results in significant patient morbidity, increases the risk for co-infection with other pathogens, and is associated with acute rejection, chronic allograft dysfunction, and increased post-transplant mortality.

Currently, a patient's risk for developing post-transplant CMV is only crudely stratified by donor and recipient serology. A majority of patients are CMV serologically positive. This means they were previously exposed to CMV and are at risk for the development of recurrent infection after transplantation. Because CMV infection typically occurs in the first few months after transplantation and/or immunosuppression, it is now standard of care to provide ganciclovir prophylaxis in this early period (typically the first 6-12 months after transplantation) in an attempt to prevent infection. However, despite prophylaxis, approximately 50% of the serologically positive recipients (R+) will develop CMV after discontinuation of ganciclovir. In contrast, a small number of patients are CMV serologically negative that receive a CMV serologically positive donor organ (D+/R−). In these patients, there is an even higher risk for the development of CMV infection given that recipients have no prior CMV immunity. As such, prophylaxis is often continued longer in these patients, sometimes indefinitely if tolerated. If prophylaxis is discontinued, however, up to 75% of serological D+/R− patients will develop CMV infection.

The invention described herein provides a method to evaluate the risk of infection for an immunocompromised patient, such as a transplant recipient and the utility of determining risk for patient management.

SUMMARY

The invention described herein provides methods and kits for carrying out the methods of evaluating an immune response of a subject to an antigen to determine the risk of viral reactivation and/or infection after transplantation and/or being immunocompromised via treatment with immunosuppressive therapy or any other means. In one aspect, methods of evaluating the risk of viral infection after transplantation in a subject are provided. In another aspect, methods of determining whether an immunosuppressed subject should be treated prophylactically with an anti-microbial agent are provided.

The methods include stimulating T cells obtained from the subject with an antigen, suitably a viral antigen, in vitro and then determining whether the T cells from the subject are expressing at least three markers selected from CD107, IFN-γ, IL-2 and TNF-α in response to the antigen stimulation. The determination of the functional response of the T cells to the antigen can then be used to evaluate the risk of viral infection in the subject or to indicate whether the subject should be treated with an anti-microbial agent. The presence of T cells expressing increased levels of at least three of the markers differentially as compared with controls is indicative of a low risk of viral infection after transplantation. Subjects in which expression of at least three of the markers is not increased as compared to controls should be treated prophylactically with an anti-microbial agent.

In particular, the presence of an increased number of T cells (either CD4+ or CD8+ T cells) expressing IFN-γ, IL-2 and TNF-α and not CD107 as compared to control cells is indicative of a low risk viral infection after transplantation. In contrast, the presence of an increased number of T cells (in particular CD8+ T cells) expressing CD107 and one of either IL-2 or IFN-γ as compared to control cells is indicative of an increased risk of viral infection. Subjects with an increased risk of infection should be treated with an anti-microbial agent. Those subjects at increased or high risk of viral infection can then be managed with more aggressive or continuous treatment with anti-microbial pharmaceuticals after immunosuppression or transplantation.

In yet another aspect, kits comprising an antibody specific for IL-2, an antibody specific for IFN-γ, an antibody specific for TNF-α, and optionally an antibody for CD107 are provided. The antibodies may be labeled with a detectable label such as a fluorescent label.

DETAILED DESCRIPTION

Figure 1:
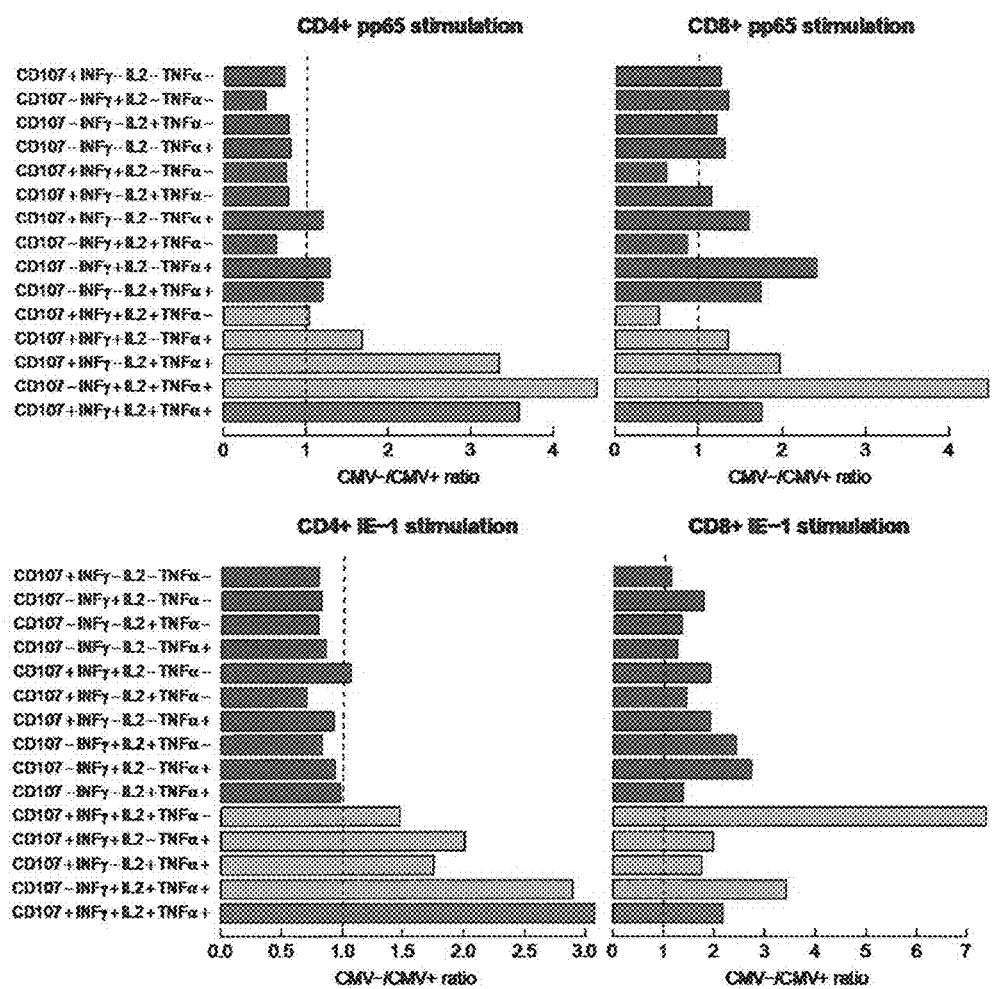
FIG. 1 is a set of graphs comparing average relative frequencies for the Boolean functional subsets in the CMV− and CMV+ groups for CD4+(left column) and CD8+ (right column) T cells under pp65 stimulation (top row) and IE-1 stimulation (bottom row) within 180 prophylaxis-free days. The CMV+ group comprises 11 patients that developed CMV during this period, while the CMV− group comprises the other 33 patients. The length of each bar represents the ratio of the mean relative frequency of the cell subset in the CMV− group to that of the same subset in the CMV+ group. A value greater than 1.0 (dashed line) indicates that the cell subset has, on average, a higher relative frequency in the CMV− group than in the CMV+ group and hence a possible immune correlate of protection. In the cell subset labels, + indicates that the cytokine is present. The color of the bar indicates the number of effector functions expressed by the cell subset, with dark green=1, blue=2, orange=3 and red=4. Higher degrees of CD4+ and CD8+ polyfunction (orange, red) occur in CMV− relative to CMV+.

Cytomegalovirus (CMV) infection and disease are some of the most common complications after solid organ transplant. In addition to the direct tissue injury of invasive disease, CMV has indirect effects including increased risk of other infections as well as organ rejection. Lung transplant recipients are at the highest risk for CMV, with a significant number of at risk patients developing infection or disease, particularly after prophylaxis ends. In a lung transplant recipient, a single episode of CMV, even with current treatments, significantly increases the risk for chronic allograft dysfunction and death.

Accordingly, international consensus guidelines recommend antiviral prophylaxis in lung transplant recipients that are pre-transplant CMV seropositive or pre-transplant CMV seronegative but receive an organ from a seropositive donor. Pre-transplant seropositive recipients represent the majority of transplants at risk for CMV. Current guidelines recommend a minimum of 6 months of antiviral prophylaxis for seropositive lung transplant recipients. However, due to the high cost of antiviral treatments such as valganciclovir, risk for bone marrow suppression and potential development of subsequent viral resistance, the optimal duration of prophylaxis is controversial, and practices vary across centers. Thus, there is an unmet clinical need to more precisely determine post-transplant risk for CMV, beyond pre-transplant recipient and donor serostatus, with the ultimate goal of tailoring CMV prophylaxis duration to an individual's specific risk.

As T cell responses are critical to CMV immune control, previous experimental assays in solid organ transplant recipients have attempted to measure T cell responses to CMV lysate or antigens to predict future infections. The QuantiFERON-CMV assay, not FDA approved in the United States but available in other countries, measures the CD8+ T cell response to HLA class I restricted CMV peptides by IFN-γ production. This enzyme-linked immunosorbent assay (ELISA) has been reported to have high specificity, but low sensitivity in organ transplant recipients. In addition, up to 30% of patients tested with QuantiFERON-CMV assay have no significant response to the positive control, making the test for specific CMV response uninterpretable. Given the absence of clinically useful and validated measures to predict future CMV, the current standard of care in seropositive lung transplant recipients is to apply a fixed duration of prophylaxis after transplantation in all patients, subjecting some to overtreatment with the risks of medication toxicity, while undertreating others that remain at higher risk for CMV.

We sought to determine if immunologic profiling of the polyfunctional CMV specific immune T cell responses could define an individual risk for CMV infection in CMV seropositive lung transplant recipients. We define polyfunctionality as individual T cells simultaneously exhibiting 3 or more immune functions in response to an antigenic stimulus. Our group has previously profiled polyfunctional T cells by flow cytometry after stimulation by CMV pp65 and by IE-1 peptide pools in immunosuppressed lung transplant recipients. See Snyder et al. Polyfunctional cytomegalovirus-specific immunity in lung transplant recipients receiving valganciclovir prophylaxis. Am J Transplant. 2011; 11(3): 553-60. We hypothesized that a polyfunctional CMV specific immune response would discriminate CMV risk and provide a novel and clinically relevant diagnostic test.

As described in the examples, a cohort of lung transplant recipients that were positive for CMV serologically were used to assess the CMV T cells and correlate the T cells with CMV reactivation. In the discovery cohort, T cell polyfunctionality was assessed by CD107a, IFN-γ, TNF-α, and IL-2 expression after CMV pp65 or IE-1 peptide stimulation. A Cox proportional hazards model was used to define the optimal predictive profile for the development of future CMV infection. Additional validation was performed. Twelve of the forty-four recipients in the discovery cohort developed CMV infection. A specific CD4+ and CD8+ polyfunctional response provided a robust model that strongly predicts risk of CMV infection. The model remained predictive in both cross validation and external validation. We identified and validated specific polyfunctional T cell signatures in response to CMV antigen stimulation that provide a clinically useful prediction of subsequent CMV risk. This novel diagnostic approach could inform the optimal duration of prophylaxis tailored to the individual, thereby reducing CMV infection after lung transplantation or other immunosuppression.

An accepted method for assessing multiple T cell functions simultaneously is the intracellular staining (ICS) assay with polychromatic flow cytometry (PFC). As shown in the Examples, the presence of polyfunctional memory T cells in subjects was predictive of subjects with a low risk of developing a viral infection after transplantation. In contrast, subjects having T cells expressing CD107 and one of either IL-2 or IFN-γ were at higher risk of developing a viral infection after transplantation. In particular, subjects with T cells (CD4+ or CD8+) expressing IFN-γ, IL-2, and TNF-α, but not expressing CD107 were unlikely to experience CMV infection after transplantation. On the other hand, subjects with T cells (in particular CD8+ T cells) expressing CD107 and IFN-γ, but not expressing IL-2 and TNF-α were likely to experience CMV infection after transplantation.

Methods of evaluating the risk of viral infection after transplantation or immunosuppression in a subject by analyzing the T cell response to in vitro stimulation with viral antigens are provided. In the methods, the T cells are stimulated with viral antigens and then the expression of CD107, IFN-γ, IL-2 and TNF-α in the T cells is assessed. Subjects having T cells expressing at least three of the four markers at higher levels after stimulation with the viral antigen as compared to control cells or cells from the subject not stimulated with the viral antigen are at lower risk of a viral infection post-transplantation. Subjects with the lowest risk of viral infection had T cells expressing all three cytokines, but were negative for CD107 expression. Subjects having T cells expressing CD107 and at least one of IL-2 or IFN-γ as compared to control cells or cells from the subject not stimulated with the viral antigen are at higher risk for developing a viral infection post-transplantation. The method may be used to calculate the risk of CMV infection as follows: log(hazard ratio)=$-0.396X_1-0.324X_2+0.307X_3$ where $X_1$, refers to the polyfunctional CD107−/IFN-γ+/IL2+/TNFα+CD4+ T cells, $X_2$ to the polyfunctional CD107−/IFN-γ+/IL2+/TNFα+CD8+ T cells, and $X_3$ to the bifunctional CD107+/IFN-γ+/IL2−/TNFα−CD8+ T cells. Based on the calculated risk, subjects with a log risk score of −1.6, −1.5, −1.4, −1.2, −1.0, −0.8, −0.6, −0.4, −0.2, 0 or more are at high risk of viral infection after transplantation or immmunosuppression. On the other hand, subjects having a calculated log risk score of CMV infection of 0, −0.2, −0.4, −0.6, −0.8, −1.0, −1.2, −1.4, −1.5, −1.6 or less are a relatively low risk of viral infection after transplantation or immunosuppression. As shown in the examples, a threshold of −1.2 is optimal with respect to the training data for minimizing misclassification. Thresholds in the range of −1.4 to 0.0 give a concordance index that falls within 1 standard error of the optimal concordance index. Those of skill in the art may make more or less conservative thresholds within this range depending on the medical context.

Methods of determining whether a subject should be treated prophylactically with an anti-microbial agent are also provided herein. Suitable subjects may be those expected to undergo a transplant operation, recent transplant recipients, those receiving immunosuppressive therapy or whose immune systems are suppressed for any reason. The subjects are generally seropositive for the antigen or the microbial source of the antigen. The methods include obtaining a sample containing T cells from the subject; stimulating the T cells obtained from the subject with an antigen in vitro; determining the expression levels of at least three markers selected from CD107, IFN-γ, IL-2 and TNF-α in response to the antigen stimulation of the T cells; and determining whether the subject should be treated with the anti-microbial agent. Subjects whose T cells respond to the antigen by expressing less than three of the markers are likely to benefit from treatment with the anti-microbial agent. Subjects whose T cells respond to the antigen by expressing at least three of the markers are unlikely to experience reactivation and/or infection with the microbe and thus may not benefit from prophylactic treatment with the anti-microbial. These subjects can avoid prophylactic treatment with the anti-microbial agent.

Also provided are methods of treating subjects to prevent viral infection post-transplantation. These methods include determining the subject's risk of viral infection post-transplantation and then treating subjects with a high risk of viral infection with an anti-viral pharmaceutical, such as ganciclovir or maintaining treatment with the anti-viral for a longer period of time than is standard treatment after transplantation or immunosuppression. The subjects having a calculated log risk score of CMV infection of −1.6, −1.5, −1.4, −1.2, −1.0, −0.8, −0.6, −0.4, −0.2, 0 or more being treated with an anti-viral for extended periods of time. For example, subjects with a higher calculated risk score than the chosen cut-off value may be prophylactically treated with anti-microbial agents for 3, 4, 5, 6, 8, 10, 12 or more months after immunosuppression or transplantation. The subjects having a calculated log risk score of CMV infection of 0, −0.2, −0.4, −0.6, −0.8, −1.0, −1.2, −1.4, −1.5, −1.6 or less do not need extended treatment with an antiviral or any antiviral treatment after transplantation. For example, subjects with a lower calculated risk score than the cut-off value selected may be treated for a shorter time or avoid treatment with an anti-microbial agent altogether.

The methods may be useful for evaluating the risk of any viral infection capable of reactivation after transplantation. In the Examples, the risk of cytomegalovirus (CMV) was evaluated, but other viruses including but not limited to other herpesviruse such as Epstein-Barr virus (EBV), varicella zoster virus or Herpes Simplex virus (HSV) may be evaluated. The antigen can be any antigen associated with the virus. Suitably the viral antigen is an antigen known to elicit a strong immune response in subjects. In the Examples, CMV pp65 and IE-1 were used. Those skilled in the art can identify appropriate viral antigens for use in the methods.

The T cells may be obtained from the subject using methods known to those skilled in the art. In the Examples, peripheral blood was used as a source of T cells, but other sources may be used. The T cells may be isolated from the peripheral blood using methods known in the art or the method provided in the Examples. As shown in the Examples, the T cells need not be purified in the sample from the subject. An anti-coagulant can be added to the peripheral blood to avoid the need to purify the lymphocytes from the blood. Heparin is an appropriate anti-coagulant. Appropriate co-stimulatory and antigen presenting cells may be included in the stimulation as well. Co-stimulatory molecules may include antibodies to CD28 or CD49d. The amount of viral antigen added can be determined by those skilled in the art but may range from 0.1 μM to 1000 μM. The T cells used in the stimulation may be CD4+ T cells, CD8+ T cells or a combination thereof. The stimulation period may be as little as 3 hours or for up to 48 hours. Suitably, the stimulation time is 4, 5, 6, 8, 10, 12, 16. 20, 24, 30, 36, or 42 hours. Suitably the stimulation is between 4-6 hours in duration.

The methods may be performed on subjects positive for the virus or for exposure to viral antigens prior to transplantation or immunosuppression. The subject may test positive for antibodies specific for the virus. The antibodies may be directed to the same antigen as the viral antigen used in the stimulation, but need not be the same. The methods may also be useful in subjects where the recipient of the transplant is negative for prior exposure to the virus, but the donor tests positive for exposure to the virus. The methods may be used and the T cells obtained from the subject before the transplantation, during the transplantation procedure or at any time after transplantation. The transplantation is generally a solid organ transplant, but the method may be useful for transplantations including but not limited to lung, liver, kidney, pancreas, small intestine, heart, bone marrow, composite tissue and corneal transplantations. In cases of immunosuppression, the immunosuppression may be naturally occurring, for example due to infection with HIV or may be pharmaceutically induced, for example in transplant patients or individuals with an autoimmune disease. Those of skill in the art will envisage subjects that may benefit from assessment of viral immune status.

The subjects are generally human subjects, but animal subjects such as mammals, including dogs, cats, horses may also be subjects within the scope of the invention.

After in vitro stimulation with the viral antigen, the T cells are assayed to determine whether the cells are expressing increased amounts of at least three markers selected from IL-2, IFN-γ, TNF-γ and CD107 as compared to controls. The T cells may be assayed for all four of the markers simultaneously or only three of the markers. The controls can be cells not stimulated with the viral antigen or can be a control profile. The expression of the at least three markers in T cells can be assayed using intracellular cytokine staining (ICS) and polychromatic flow cytometry (PFC). This method of assaying single cells for multiple markers is well known in the art. Other methods may also be utilized, such as immunofluorescence or ELISPOT assays, but the number of markers assayed for a single cell is more limited in these methods. ELISA may be useful for some markers that do not need to be evaluated on a cell-by-cell basis. The key is determining whether the subject has a higher number of polyfunctional T cells responsive to the virus antigen as compared to controls. Those subjects with a polyfunctional T cell response are less likely to have a viral infection after transplantation or immunosuppression.

The ICS and PFC method uses Brefeldin A or another secretion inhibitor to concentrate the amount of the cytokines induced by the antigen stimulation within the cells such that the expression of secreted molecules can be more readily determined. After stimulation, the cells are harvested, fixed and permeabilized using methods known to those skilled in the art. The cells are then incubated with antibodies specific for the at least three markers and may also be incubated with antibodies for additional markers such as CD4, CD8, CD3, CD69 or other markers to identify and characterize the T cells after stimulation. The antibodies may be labeled for detection in a fluorescence activated cell sorter (FACS). Suitably the antibodies are differentially labeled to allow for simultaneous evaluation of the at least three markers in the stimulated cells.

The expression patterns of at least three markers in and/or on the T cells of a subject after stimulation with the viral antigen are predictive of the likelihood of viral infection in the subject after transplantation or immunosuppression and the associated morbidity and/or mortality that can result from the viral infection. Subjects with T cells capable of expressing IL-2, IFN-γ and TNF-α after stimulation with a relevant antigen are at low risk of viral infection after transplantation or immunosuppression. The T cells from these low risk subjects may not express CD107. Subjects expressing CD107 in combination with IL-2, IFN-γ and TNF-α on CD4+ cells are at an even lower risk of infection. Those at low risk of infection need not be treated with anti-microbial agents or can be treated for a shorter period of time. Alternatively, if CD8+ T cells express CD107 in combination with IL-2, IFN-γ and TNF-α, then the risk of infection is increased relative to CD8+ T cells expressing the cytokines, but not CD107. Thus subjects with increased CD8+ T cells expressing CD107, IL-2, IFN-γ and TNF-α should be treated with the anti-microbial agent prophylactically. Subjects with T cells expressing CD107 and only one of IFN-γ or IL-2, and not expressing TNF-α, are at high risk of viral infection after transplantation or immunosuppression. Subjects with T cells expressing only one of the markers are also at increased risk of infection and should be treated with the anti-microbial agent prophylactically.

A high risk of viral infection means that the subject is at least 20%, 30%, 40%, 50%, 60%, 70%, 80%, 90% or even 100% more likely to develop a viral infection after transplantation or immunosuppression than the population of transplantation recipients or immunosuppressed subjects as a whole. A low risk of viral infection means that the subject is at least 20%, 30%, 40%, 50%, 60%, 70%, 80%, 90% or even 100% less likely to develop a viral infection after transplantation or immunosuppression than the population of transplantation recipients or immunosuppressed subjects as a whole. Subjects determined to be at high risk of viral infection may be treated with an anti-microbial pharmaceutical or may be treated for a longer duration with the anti-microbial pharmaceutical than would be the normal standard of care. Subjects determined to be at low risk of viral infection may not be treated with an anti-microbial pharmaceutical or may be treated for a shorter duration with the anti-microbial pharmaceutical than would be the normal standard of care. Suitably anti-microbial agents include but are not limited to ganciclovir, valganciclovir, foscarnet, acyclovir, cidofovir, maribavir and leflunomide.

Treating the subject includes, but is not limited to, reducing the severity or duration of viral infection in the subject, lengthening the disease free and/or prophylaxis free time period in the subject, reducing the likelihood of recurrence of the virus or reducing the chance that the transplanted organ will fail in a subject. Treating a subject as used herein refers to any type of treatment that imparts a benefit to a subject. The subjects may be treated with any anti-viral known in the art and those of skill in the art can determine the appropriate dose and duration of treatment.

Kits for performing the methods of the invention are also provided. The kits include at least two of an antibody specific for IL-2, an antibody specific for IFN-γ and an antibody specific for TNF-α. The kits suitably contain all three antibodies. The kits may further include an antibody specific for CD107 or additional antibodies specific for additional markers such as CD4, CD8, CD3, CD45RO, CD27, CD57 or CD69. The antibodies may be labeled, suitably with different fluorescence labels for use in PFC assays. The kits may further include reagents and instructions necessary to perform the methods such as heparin, brefeldin A, fixation and permeabilization reagents.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

Examples

Results

Study cohort: The discovery cohort included 44 CMV serologically positive lung transplant recipients as outlined in Table 1. The demographic features and indications for transplant reflect the lung transplant population at Duke University Medical Center. Cross sectional blood draws were obtained a median of 363 days after transplant (IQR 205, 628). These recipients were followed for at least one year of prophylaxis-free days post blood draw. Three recipients died during the follow-up period. The median number of prophylaxis days posttransplant was 364 (IQR 153, 477). The median prophylaxis-free follow-up time, as calculated by the reverse Kaplan-Meier method (Shuster JJ. Median follow-up in clinical trials. Journal of clinical oncology: official journal of the American Society of Clinical Oncology. 1991; 9(1):191-2) was 539 days (95% CI: 502-777 days). A separate validation cohort included 18 recipients who received posttransplant prophylaxis for a median of 532 days (IQR 394.8-701.0) and had a reverse Kaplan-Meier estimate of the median prophylaxis-free follow-up of 154 days (95% CI: 151-274).

TABLE 1

The clinical and demographic characteristics of the 44 serologically CMV positive lung transplant recipients within the Discovery Cohort. CMV is defined as DNAemia or Pneumonia.

|  | Developed CMV* N = 12 N (%); median (IQR) | No CMV N = 32 N (%); median (IQR) |
|---|---|---|
| Male | 8 (67) | 15 (47) |
| Age at Transplant | 68 (62, 71) | 66 (59, 68) |
| Race |  |  |
| Caucasian | 11 (92) | 30 (94) |
| African-American | 1 (8) | 2 (6) |
| Indication for Lung Transplant |  |  |
| Obstructive Disease | 6 (50) | 9 (28) |
| Restrictive Disease | 6 (50) | 20 (63) |
| Cystic Disease | 0 (0) | 2 (6) |
| Vascular Disease | 0 (0) | 1 (3) |
| Lung Transplant Operation |  |  |
| Bilateral | 7 (58) | 18 (56) |
| Single | 5 (42) | 14 (44) |
| Patients on Prophylaxis at Blood Draw | 5 (42) | 12 (38) |
| Prophylaxis Days | 254 (148, 365) | 373 (232, 545) |
| Prophylaxis Strata |  |  |
| ≤90 d | 0 (0) | 0 (0) |
| >90-≤180 | 2 (17) | 8 (25) |
| 180-365 d | 10 (83) | 7 (22) |
| >365 | 0 (0) | 17 (53) |
| Days from Transplant to Blood Draw | 342 (147, 419) | 400 (215, 667) |

*all 12 had DNAemia; only one subject had concurrent pneumonia

Development of CMV infection and/or disease: In the discovery cohort of 44 lung transplant recipients, 12 developed CMV DNAemia, with one developing concurrent CMV pneumonitis. Eleven of the 12 recipients developed CMV DNAemia during the first 180 prophylaxis-free days.

In the validation cohort, three recipients developed CMV DNAemia during follow-up (Table 2).

TABLE 2

Demographics of the Validation Cohort
Demographic & Clinical N = 18

| | N (%); median (IQR) |
|---|---|
| Gender, Male | 9 (50) |
| Age at Transplant | 62 (56, 65) |
| Race: | |
| Caucasian | 15 (100) |
| African-American | 0 (0) |
| Indication for Lung Transplant | 6 (33) |
| Obstructive | 10 (56) |
| Restrictive | 2 (11) |
| Cystic | 0 (0) |
| Vascular | |
| Lung Transplant Operation | |
| Bilateral | 11 (61) |
| Single | 7 (39) |
| Patients on Prophylaxis at Blood Draw | 18 (100) |
| Prophylaxis Days | 532 (395, 701) |
| Total Prophylaxis Strata | |
| ≤90 d | 0 (0) |
| >90-≤180 | 0 (0) |
| 180-365 d | 3 (17) |
| >365 | 15 (83) |
| Days from TX to Blood Draw | 131 (78, 234) |

Polyfunctional T cell assessment and subsequent CMV: To determine whether T cell polyfunctionality is predictive of protection from CMV in transplant patients, we examined CD107a expression in addition to performing intracellular cytokine staining for IFN-γ, TNF-α, and IL-2 following stimulation of PBMC with pools of CMV pp65 or IE-1 peptides. Initial graphical comparison for the discovery cohort was performed using the average relative frequencies for the functional subsets in recipients who developed CMV during the first 180 days of prophylaxis-free follow up compared to all other patients as shown in FIG. 1. Of note, there were 4 subjects that did not have 180 prophylaxis-free days and 1 subject developed CMV after 180 prophylaxis-free days that were included as CMV-(n=33). Comparing those that did not prophylaxis-freedevelop CMV to those that did develop CMV within 180 prophylaxis-free days, the highest ratios of the mean relative frequencies were found in subsets expressing at least 3 of the markers (CD107a, IFN-γ, TNF-α, IL-2). This indicates a role of polyfunctional T cells in protecting against CMV infection.

Development of a CMV risk prediction score: As described in the Methods, a Cox proportional hazards regression model for prophylaxis-free follow up time to CMV infection using the log ratios of stimulated to unstimulated cell subset relative frequencies as covariates was used. All recipients that developed CMV at any time point were included (n=12) and all recipients without CMV (n=32) were included with all available follow up. Covariates from the CMV pp65 stimulation (cross-validation concordance index=0.84 with SE 0.019) were found to be most predictive and superior to a model using covariates from IE-1 stimulation (cross-validation concordance index=0.79 with SE 0.019). The analysis also considered if maturational markers might distinguish those at risk for CMV in addition to the intracellular cytokine markers. Using maturational markers in both CD4+ and CD8+ subsets as model covariates (cross-validation concordance index=0.83 with SE 0.02) did not improve the prediction of subsequent CMV over the CMV pp65 basic cell subset model alone.

After adaptive LASSO shrinkage, only 3 cell subsets in the CMV pp65 stimulation condition were found to have non-zero coefficients. The final model derived from this analysis to calculate CMV risk is as follows: log(hazard ratio)=−0.396$X_1$−0.324$X_2$+0.307$X_3$ where $X_1$, refers to the polyfunctional CD107−/IFN-γ+/IL2+/TNFα+CD4+ T cells, $X_2$ to the polyfunctional CD107−/IFN-γ+/IL2+/TNFα+ CD8+ T cells, and $X_3$ to the bifunctional CD107+/IFN-γ+/IL2−/TNFα−CD8+ T cells. From the estimated coefficients, the two polyfunctional cell subsets were associated with decreased risk for CMV infection while the bifunctional CD8+ T cell subset was associated with increased risk. Harrell's concordance index, a measure of model prediction performance, was 0.88 (SE=0.087).

Figure 2:
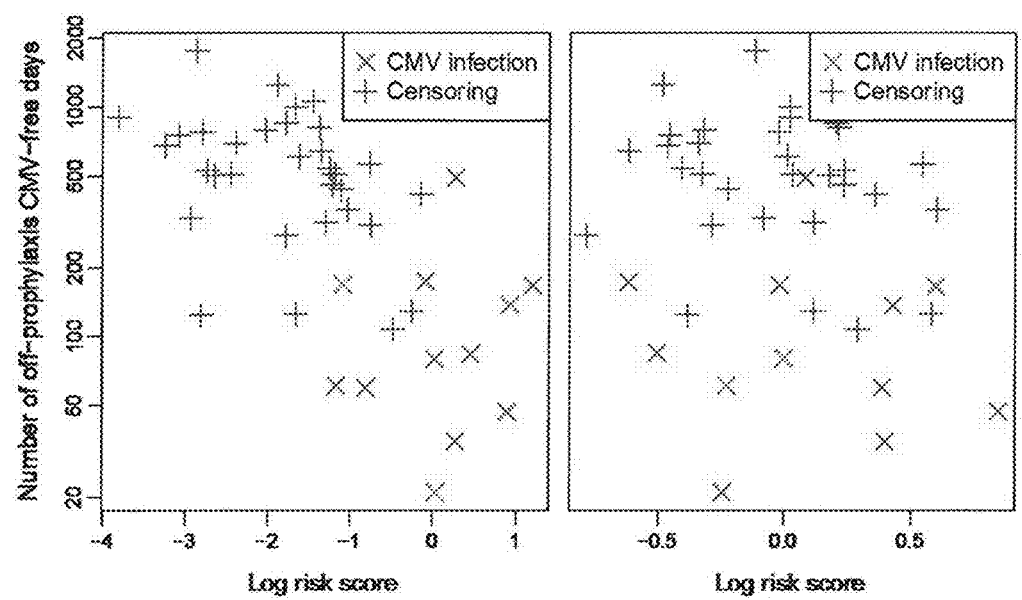
FIG. 2 is a set of graphs showing the effectiveness of log risk score (x-axis) for polyfunctional T cell subset model derived from our discovery data (left panel) and QuantiF-ERON-CMV proxy single cytokine model derived from the same data (right panel) to identify patients that develop CMV (red x) from those free of CMV (blue+), adjusted for time after completion of prophylaxis (y-axis). Patients that do not develop CMV are clearly discriminated by the polyfunctional subset model with a suitable risk score threshold but not by the proxy QuantiFERON where CMV events are distributed throughout with no risk score threshold.

Concordance between prophylaxis-free follow up time to CMV infection and risk scores based on IFN-γ versus polyfunctional cytokine production: To evaluate the predictive ability of models based only on CD8+IFN-γ+ cell subset frequencies stimulation (proxy for the QuantiFERON-CMV assay), we fitted a standard Cox regression model using only CD8+IFN-γ+ after pp65 and IE-1 stimulation as covariates. In contrast with the polyfunctional cell subset model, the concordance index was only 0.58 (SE=0.087), indicative of minimal ability to discriminate patients at low or high risk for CMV infection (FIG. 2). This indicates that polyfunctional T cell subsets provide critical prognostic information, not available with single parameter assays such as the QuantiFERON-CMV, which is essential for discrimination.

Cross-validation for concordance: To avoid over-fitting resulting from using the same data for model fitting and evaluation (resubstitution estimate), we used 10 times repeated 5-fold cross-validation to estimate the true concordance index. The estimated concordance index for the final model was 0.84 (SE=0.019) indicating that the model predictions are robust under cross-validation.

Figure 3:
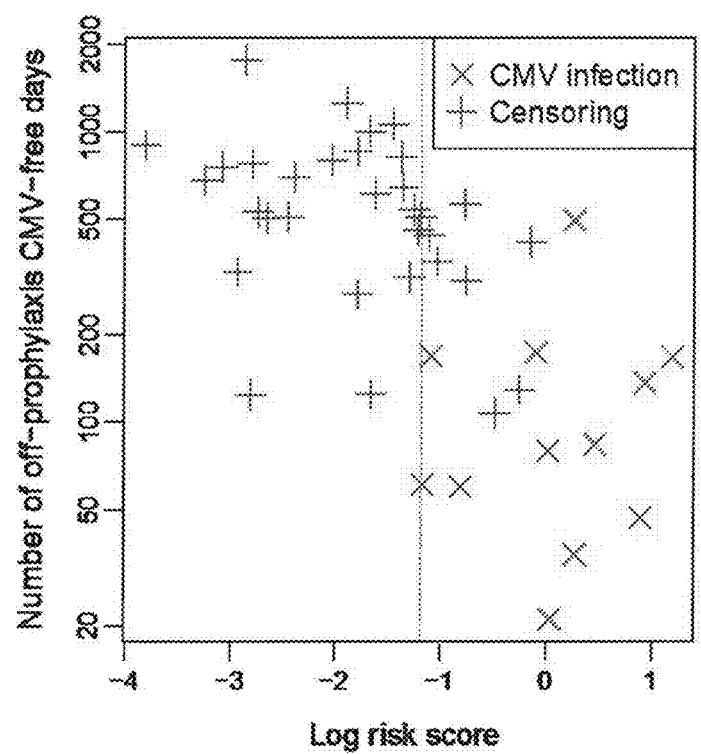
FIG. 3 is a graph showing selection of the best cutoff for log risk score in the final polyfunctional subset model derived from the discovery data. For each candidate cutoff value, log risk scores of the 44 patients were dichotomized by the given threshold and concordance index between the dichotomized log risk scores and off-prophylaxis times to CMV infection was computed. The vertical grey line is drawn at −1.2, the best cutoff that gives the highest concordance index of 0.84 (SE=0.071). This cutoff value discriminated subsequently infected CMV patients and patients that do not develop CMV. The grey shaded area is drawn over the interval [−1.4, 0.0] which include all cutoff values whose concordance indexes are within 1 SE of the largest concordance index. For more conservative withdrawal of prophylaxis, one may consider using a cutoff of −1.4.

Cut of selection: In order to establish a cut off for the log risk score to discriminate between patients at low and high risk for future CMV, we calculated the concordance between the prophylaxis-free follow-up time to event and risk score dichotomized by a given cutoff. The best cut off was determined to be a log risk score of −1.2. This cut off gave the highest concordance index. Log risk scores in the range of −1.4 to 0.0 give a concordance index that falls within 1 SE of the optimal concordance index. Hence, a more conservative estimate could consider −1.4 as the threshold. This is reflected in FIG. 3.

Figure 4:
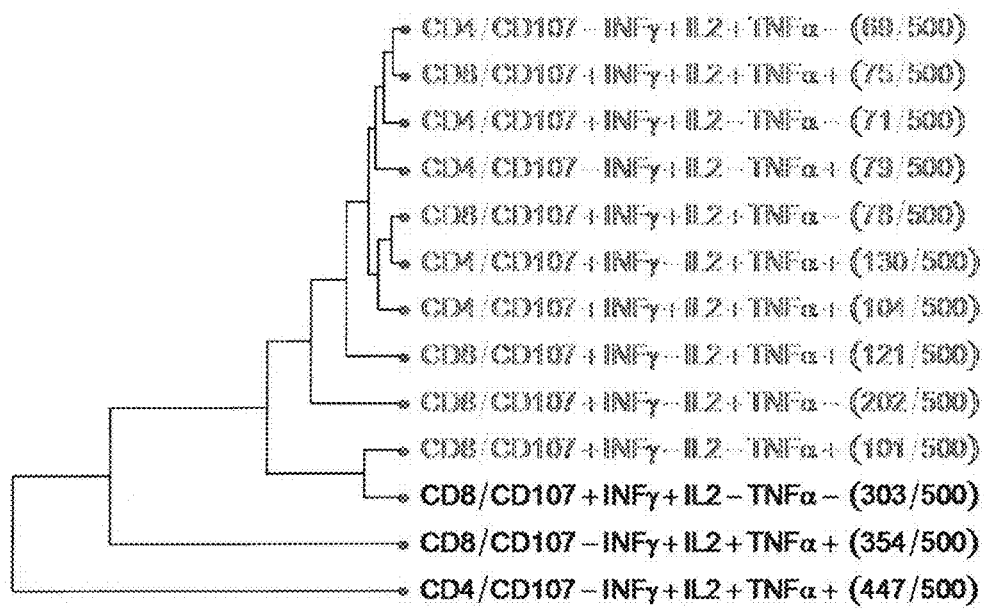
FIG. 4 is a dendrogram showing cell subset variables that have a frequency of at least 50 (10%) from 500 bootstrap samples. Hierarchical agglomerative clustering was performed with complete linkage using frequency of co-occurrence of each cell subset pair (the number of times the two cell subsets were selected together as variables) in the final bootstrap models as a distance measure. Shown in each parenthesis is frequency of occurrence of the cell subset (the number of times the cell subset was selected as a variable) in the bootstrap final models. The filled circle at each end node is colored according to the majority of the signs of the coefficient estimate for the corresponding cell subset with red indicating positive (associated with increased risk of CMV infection) and blue indicating negative (associated with decreased risk of CMV infection). Cell subsets appearing in the final model for the original data are shown in black while others in grey, and can be seen to be the most frequently selected ones and reasonable representatives of their local clusters.

Bootstrap analysis: To evaluate the stability of the putative immune correlates found using adaptive LASSO shrinkage, the procedure was repeated for 500 bootstrap samples of the discovery cohort and agglomerative hierarchical clustering was performed. From the dendrogram in FIG. 4, the three cell subsets most frequently found in the bootstrap samples are CD4+/CD107−/IFN-γ+/IL2+/TNFα+(89.4%), CD8+/CD107−/IFN-γ+/IL2+/TNFα+(70.8%), and CD8+/CD107+/IFN-γ+/IL2−/TNFα− (60.6%), the same cell subsets selected for the final model.

Figure 5:
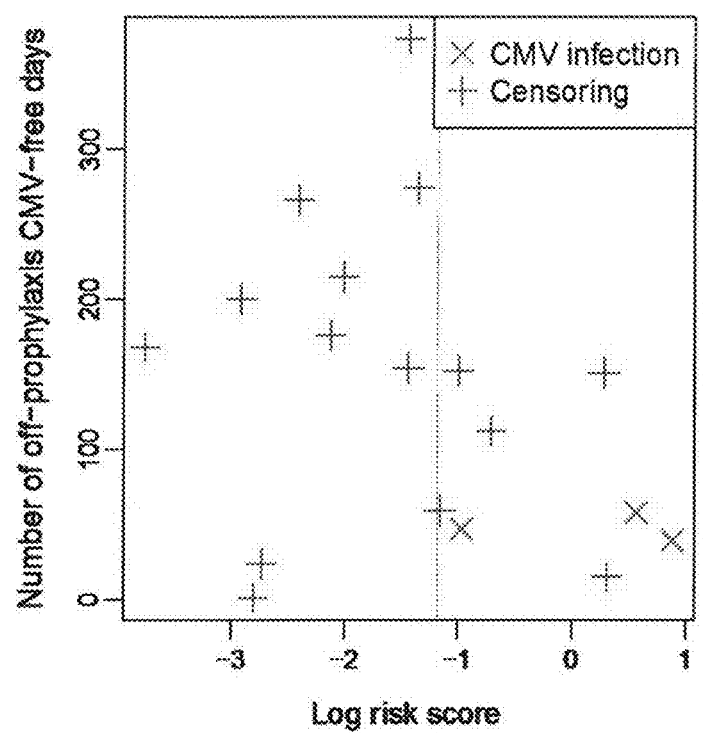
FIG. 5 is a graph showing the effectiveness of log risk score (x-axis) for polyfunctional T cell subset model derived from our validation data. Patients that do not develop CMV are clearly discriminated by the polyfunctional subset model with a log risk score less than −1.2, the best cutoff value selected from the discovery data.

External validation: After the final model was fitted, we conducted a second independent study in a cohort of 18 independent serologically positive patients with no prior CMV, on prophylaxis at the time of blood draw and subsequently stopped prophylaxis after the blood draw. Demographics of these recipients are described in supplemental table 1. Three of these recipients developed CMV infection over the follow-up period. CD4+ and CD8+ immunity to pp65 was measured as described previously and we assessed the ability of the polyfunctional subset model to predict the risk of CMV infection. The model predictions were robust in the external validation. The concordance index for this independent cohort using the final model was 0.92 (SE=0.179). The distribution of the log risk score is shown in FIG. 5.

Our novel diagnostic approach is the first to consider measures of T cell polyfunctionality in determining future CMV risk, and thus represents a major advance over existing approaches to CMV risk stratification and prevention based on a single factor analysis. Our results demonstrate that a polyfunctional approach is considerably more reliable than a single cytokine analysis, such the QuantiFERON-CMV assay, which measures CD8+ T cell IFN-γ production by ELISA in response to CMV peptides. Our mock QuantiFERON-CMV assay, limited to just IFN-γ production from CD8+ T cells after pp65 and IE-1 stimulation, did not predict future CMV events. Our conclusion is that single cytokine production is not a reliable measure of CMV specific immunity in lung transplant recipients; a finding that is supported by other studies.

Our analysis indicates that higher frequencies of both CD4+ and CD8+ polyfunctional T cells are associated with protection against CMV infection. This may be surprising given the predominant role of CD8+ in viral infections, especially for prevention and control of primary CMV disease after transplant. However, other transplant studies have indicated an important role for CD4+ T cells in CMV viral control after transplant as well.

In the current study, we explored both IE-1 and pp65 stimulation. Our analysis indicates that the model was more predictive of CMV infection risk when using data from pp65 stimulated than from IE-1 stimulated samples, even though both stimulations elicited polyfunctional T cell responses. In our present studies, a model using IE-1 data was less predictive than the model using pp65 reactivity.

Finally, an important interpretation of our results is that T cells are capable of mounting a polyfunctional cytokine response that correlates to infection risk. A polyfunctional T cell response is associated with control of both HIV-1 and HIV-2, mycobacteria tuberculosis (latent disease), hepatitis C, as well as other infections. In addition, a polyfunctional cytokine response after vaccination is considered protective. A polyfunctional signature was required to accurately and reproducibly predict those at high risk for subsequent CMV. This provides some insights into the potential mechanism by which polyfunctional cells might regulate host CMV specific immunity, as triple cytokine producing cells appear to be functionally superior in both in vitro and in vivo systems. However, additional studies are needed to more precisely define the mechanisms by which specific degrees of polyfunctionality confer protective CMV specific immunity after lung transplantation.

In conclusion, we demonstrate a unique immunological approach to improve CMV risk stratification that considers CMV-specific polyfunctional cytokine production. This novel assay could directly impact and improve clinical lung transplant care by avoiding excessive prophylaxis in some individuals and under treatment in others. By individualizing treatment, we can ultimately reduce the burden of both prophylaxis and of CMV after lung transplantation and improve long-term patient outcomes. Our results suggest that a similar approach to CMV prevention would be useful to explore across all the commonly transplanted solid organs, as well as bone marrow transplantation, since CMV remains a common and serious problem among all transplant recipients.

Methods:

Discovery and Validation Study Cohorts:

Lung transplant recipients at Duke University Medical Center who were serologically positive for CMV prior to transplant, had not yet developed posttransplant CMV infection or pneumonia and were at least 4 weeks posttransplant, were eligible for the study. All recipients had received CMV prophylaxis. Exclusion criteria included age <18, multiorgan transplant, and retransplantation. Transplant donors were either CMV serologically positive or negative. Peripheral whole blood samples for the research assays were collected at the time of clinical sample collection. Recipients were followed prospectively for development of CMV DNAemia and pneumonia occurring after the blood sample collection date. Discovery and validation subjects were concurrently recruited with the validation cohort samples stored for later analysis. All subjects signed consent to participate in the IRB approved protocol (Pro00007005).

Clinical Protocol Management:

At the time of transplant, induction immunosuppression included methylprednisolone and basiliximab. Maintenance immunosuppression included tacrolimus, corticosteroids and either mycophenolate mofetil or azathioprine. Immunosuppression was adjusted based on white blood cell count, intolerance to side effects, infection, rejection history, and renal function. All recipients serologically positive for CMV prior to transplant received intravenous ganciclovir after transplant. Once oral medications were restarted, recipients were then changed to oral valganciclovir and continued on valganciclovir for up to one year post transplant, per center protocol. CMV prophylaxis was discontinued prior to one year for leukopenia or due to patient cost.

Sample Collection and Storage of Peripheral Blood Mononuclear Cells

Peripheral blood draw was obtained by venipuncture and collected in acid-citrate-dextrose tubes (BD Vacutainer, Franklin Lakes, N.J.). Peripheral blood mononuclear cells were isolated within 6 hours of blood draw by Ficoll density gradient, washed and counted. Cells were resuspended in cryoprotectant consisting of 90% FBS (Gemini, West Sacramento, Calif.) and 10% DMSO (Sigma, St Louis, Mo.). The cell suspension was then progressively cooled to −80° C. overnight and subsequently stored in vapor phase liquid nitrogen. Prior studies by our group comparing fresh and cryopreserved peripheral blood mononuclear cells have shown recovery to be consistently above 80% viable lymphocytes and with no significant differences in antigen-specific functional reactivity.

Cell Preparation, Stimulation and Flow Cytometry in Assessing CMV Specific Immunity Viably cryopreserved cells were thawed, washed and rested overnight in RPMI (Gibco, Carlsbad, Calif.) containing 10% FBS (Cell Generation, Fort Collins, Colo.) and 1% penicillin/streptomycin/glutamine (Gibco) at 37° C. in a 5% $CO_2$ incubator. For each subject, $2 \times 10^6$ PBMCs were separately stimulated with CMV pp65 peptide pool (JPT Peptide Technologies, Berlin, Germany)+costimulatory molecules anti-CD28 and anti-CD49d (BD Biosciences, San Jose, Calif.) or with an IE-1 peptide pool (JPT Peptide Technologies)+costimulatory molecules anti-CD28 and anti CD49d. CMV peptide pools spanned the entire target region (pp65 or IE-1) in 15 amino acid peptides, overlapping by 11 amino acids and used at a concentration of 1 µg/mL. A negative control (costimulatory molecules anti-CD28 and anti CD49d alone) and a positive control with staphylococcal enterotoxin B (Sigma)+costimulatory molecules anti-CD28 and anti-CD49d were included for each subject. Brefeldin-A (Sigma) at a concentration of 5 μg/mL, Monensin (BD Biosciences) at a concentration of 1 ug/mL, and anti-CD107a PE-Cy5 (BD Biosciences) were added to the stimulation mixes prior to incubation for 6 hours at 37° C., then 4° C. overnight. The following day, EDTA (FastImmune, BD) was added to the samples. After an incubation period, the cells were washed and then incubated with a cell surface antibody mix of anti-CD3 AmCyan, anti-CD4 PerCP-Cy5.5, anti-CD8 APC-Cy7, and anti-CD14 PacBlue, anti-CD27 APC, anti-CD57 (BD Biosciences), anti-CD45RO (Beckman Coulter) and Live/Dead Fixable Violet Dye (Invitrogen). Following this incubation, the cells were washed, lysed (FACSLysing Solution, BD Biosciences) and permeabilized (FACSPermeabilizing Solution. BD Biosciences) according to the manufacturer's instructions. The cells were then incubated with an intracellular antibody mix of anti-IL-2 PE, anti-TNFα Alexa700, and anti-IFN-γ PE-Cy7 (BD Biosciences). After incubation, the cells were washed and cell pellets fixed in 1% formalin. Compensation beads (BD Biosciences) were stained with monoclonal antibodies and used to determine compensation. Data was acquired immediately with a LSRII flow cytometer (BD Biosciences).

Assessment of CMV Infection and Disease

Serial blood draws with CMV detection by PCR are done as part of routine clinical care at 1, 3, 6, 9 and 12 months posttransplant and every 3 months thereafter. Additional testing is performed if a CMV seropositive recipient stops prophylaxis prior to 1 year posttransplant. CMV DNAemia was defined as having ≥250 copies/ml of viral DNA detected in the peripheral blood. Prophylaxis-free follow up days was determined by totaling the number of days off prophylaxis until CMV event date, study censor date (Sep. 10, 2013) or death date. The days off prophylaxis did not need to be contiguous.

Surveillance transbronchial biopsies are done at 1, 3, 6, 9 and 12 months post-transplant and then annually thereafter. Additional biopsies are performed as clinically indicated and to follow up on rejection. Immunohistochemistry was prospectively performed on all transbronchial lung biopsies with CMV pneumonitis defined by positive IE-1 immunohistochemistry.

Statistical Approach

Raw flow cytometry data was analyzed by a sequential gating strategy and Boolean gating using FlowJo analysis software (Ashland, Oreg.). For the flow data statistical analysis, the relative frequencies of cell subsets relative to the total CD3 count were used. To correct for possible variations in background, functional expression levels were addressed by using log (base 2) ratios of the cell subset relative frequencies in the stimulation condition to those in the negative control (costimulation only). In an initial descriptive analysis, recipients were categorized as CMV+ or CMV− in the first 180 prophylaxis-free days. Recipients without 180 prophylaxis-free days were categorized as CMV−.

In order to develop a CMV risk prediction model that takes into account time-to-event, the primary outcome variable was set as the number of prophylaxis-free follow up days to either study censor date or the date of detection of CMV infection or disease. We then fitted a Cox regression model using the adaptive LASSO optimizer (a covariate selection strategy) for these time-to-event outcomes against the log ratios. See Zou H. The Adaptive Lasso and Its Oracle Properties. Journal of the American Statistical Association. 2006; 101:1418-29; Tibshirani R. The lasso method for variable selection in the Cox model. Statistics in medicine. 1997; 16(4):385-95; Tibshirani R. Regression Shrinkage and Selection via the Lasso. Journal of the Royal Statistical Society. 1996; 58(1):267-88.

In the initial step, the best standard LASSO fit, our choice for generating adaptive weights, was found by leave-one-out cross-validation and absolute values of the corresponding coefficient estimates were obtained to be inversely used as adaptive weights in the adaptive step. In the adaptive step, using these adaptive weights, the best adaptive LASSO parameter was then found by another leave-one-out cross-validation and the resulting best adaptive LASSO fit was chosen as the final model. The adaptive LASSO optimizer not only greatly reduced the number of variables in the final model, but also provided shrinkage estimates that are more stable than the non-regularized version. Each of the initial and adaptive LASSO steps was performed using the 'glmnet' package (Friedman et al., Regularization Paths for Generalized Linear Models via Coordinate Descent. Journal of statistical software. 2010; 33(1):1-22 and Simon N, Friedman J, Hastie T, Tibshirani R. Regularization Paths for Cox's Proportional Hazards Model via Coordinate Descent. Journal of statistical software. 2011; 39(5):1-13) in the R statistical software that implements penalized Cox regression based on coordinate-wise descent optimization.

A bootstrap analysis was done with 500 model fits to confirm the robustness of the initial polyfunctional model variables. For each bootstrap sample of the discovery cohort, the best adaptive LASSO was found by leave-one-out cross-validation as in the main analysis. We then counted the number of times each pair of variables was selected together. Since LASSO tends to choose one of highly correlated variables, variables selected together are not likely to be strongly correlated. Using this count as a dissimilarity measure, we performed hierarchical clustering with complete linkage and created a dendrogram to see what other cell subsets would have been selected in the final model if the data were slightly different.

Once the final polyfunctional model was established, we compared it in discriminatory ability with a model just using the CD8+ IFN-γ data, as utilized in the QuantiFERON-CMV assay. The concordance index (See Harrell et al. Multivariable prognostic models: issues in developing models, evaluating assumptions and adequacy, and measuring and reducing errors. Statistics in medicine. 1996; 15(4):361-87), a measure of the agreement between log risk score and time to CMV infection, was used to compare performance of the polyfunctional and single cytokine models.

Since the resubstitution estimates for the concordance index are optimistic as predictions are made on the same data used to build the model, we used cross-validation to estimate the true concordance index. The cross-validation concordance index was calculated as average of the concordance index for the 50 repetitions in 10 times repeated stratified 5-fold cross-validation. Within each training set of the cross-validation, (internal) leave-one-out cross-validation was used for tuning adaptive LASSO parameters.

We claim:

1. A method of treating a subject with an anti-microbial agent comprising:
(a) obtaining a sample containing T cells from the subject;
(b) stimulating the T cells obtained from the subject with an antigen in vitro; (c) determining an expression level of at least three markers selected from CD107, IFN-γ, IL-2 and TNF-α in response to the antigen stimulation of the T cells; (d) evaluating a risk of infection in the subject based on the expression of the at least three markers selected from CD107, IFN-γ, IL-2 and TNF-α in each of the T cells, and (e) treating the subject with the anti-microbial agent for a duration based on the risk of infection, wherein when the number of T cells expressing at least three of the markers is lower than in controls, the subject is at high risk of infection.

2. A method of treating an immunosuppressed subject with an anti-microbial agent comprising: (a) obtaining a sample containing T cells from the immunosuppressed subject; (b) stimulating the T cells obtained from the subject with an antigen in vitro; (c) determining an expression level of at least three markers selected from CD107, IFN-γ, IL-2 and TNF-α in each of the T cells in response to the antigen stimulation of the T cells; (d) determining whether the immunosuppressed subject should be treated with the anti-microbial agent based on the expression of the at least three markers selected from CD107, IFN-γ, IL-2 and TNF-α in each of the T cells; and (e) treating the subject with the anti-microbial agent if it is determined that the subject should be treated with the anti-microbial agent, wherein expression of less than three of the markers indicates the subject would benefit from treatment with the anti-microbial agent.

3. The method of claim 2, wherein the antigen is from cytomegalovirus (CMV).

4. The method of claim 3, wherein the viral antigen is cytomegalovirus (CMV) pp65 or immediate-early protein 1 (IE1).

5. The method of claim 2, wherein the subject is a candidate for or has received a transplant.

6. The method of claim 5, wherein the transplant is a transplantation selected from the group consisting of lung, liver, heart, kidney, pancreas, small intestine, composite tissue, bone marrow and corneal.

7. The method of claim 2, wherein the subject has antibodies for the viral antigen.

8. The method of claim 2, wherein the sample is a peripheral blood sample.

9. The method of claim 8, wherein the T cells are isolated from the peripheral blood sample prior to the stimulation.

10. The method of claim 2, wherein the T cells are CD4+ T cells or CD8+ T cells.

11. The method of claim 10, wherein antigen presenting cells are added with the antigen.

12. The method of claim 2, wherein subjects with T cells expressing levels of IL-2, IFN-γ and TNF-α higher than controls are at low risk for infection after immunosuppression.

13. The method of claim 12, wherein the T cells do not express CD107.

14. The method of claim 12, wherein the T cells are CD4+ T cells.

15. The method of claim 2, wherein subjects with T cells expressing is determined only CD107, of IFN-γ and IL-2.

16. The method of claim 1, wherein step (d) comprises calculating the risk of CMV infection as follows: log(hazard ratio)=$-0.396X_1-0.324X_2+0.307X_3$ where a $X_1$, refers to the polyfunctional CD107−/IFN-γ+/IL2+/TNFα+CD4+ T cells, a $X_2$ to the polyfunctional CD107−/IFN-γ+/IL2+/TNFα+CD8+ T cells, and a $X_3$ to the bifunctional CD107+/IFN-γ+/IL2-/TNFα-CD8+ T cells.

17. The method of claim 16, wherein the duration is longer than would be the normal standard of care when the subject has a risk of CMV infection with a log risk score greater than −1.2.

18. The method of claim 1, wherein the duration of treatment with the anti-microbial agent is determined by the risk of infection such that if the risk of infection is high, the duration of treatment is longer than would be a standard of care; and if the risk of infection is low, the duration of treatment is shorter than would be the normal standard of care.

19. A method of treating a subject with an anti-microbial agent comprising:
(a) obtaining a sample containing T cells from a subject;
(b) stimulating the T cells obtained from the subject with an antigen in vitro; (c) determining an expression level of at least three markers selected from CD107, IFN-γ, IL-2 and TNF-α in response to the antigen stimulation of the T cells in the sample; and (d) treating the subject with an anti-microbial agent when the number of T cells expressing at least three of the markers is lower than in controls.

* * * * *